United States Patent
Han et al.

(10) Patent No.: US 8,021,038 B2
(45) Date of Patent: Sep. 20, 2011

(54) METHOD FOR IDENTIFYING A BIOMOLECULE

(75) Inventors: Jung-Im Han, Yongin-si (KR); Jeo Young Shim, Yongin-si (KR); Won Seok Chung, Hwaseong-si (KR); Kak Knamkoong, Seoul (KR)

(73) Assignee: Samsung Electronics Co., Ltd. (KR)

( * ) Notice: Subject to any disclaimer, the term of this patent is extended or adjusted under 35 U.S.C. 154(b) by 818 days.

(21) Appl. No.: 12/108,686

(22) Filed: Apr. 24, 2008

(65) Prior Publication Data

US 2009/0122828 A1 May 14, 2009

(30) Foreign Application Priority Data

Nov. 8, 2007 (KR) .................. 10-2007-0113958

(51) Int. Cl.
*G01N 25/00* (2006.01)
(52) U.S. Cl. ................. 374/10; 374/21; 374/178
(58) Field of Classification Search ............ 374/10, 374/21, 43, 45, E17.001, E7.035
See application file for complete search history.

(56) References Cited

U.S. PATENT DOCUMENTS

| | | | |
|---|---|---|---|
| 4,238,757 A | 12/1980 | Schenck | |
| 4,777,019 A | 10/1988 | Dandekar | |
| 6,567,763 B1* | 5/2003 | Javanifard et al. | 374/173 |
| 2003/0013103 A1* | 1/2003 | Bryan et al. | 435/6 |
| 2004/0214312 A1* | 10/2004 | Tyvoll et al. | 435/288.4 |
| 2006/0071700 A1* | 4/2006 | Meyer et al. | 327/512 |
| 2007/0045756 A1* | 3/2007 | Chang et al. | 257/414 |
| 2007/0243642 A1* | 10/2007 | Miyata | 374/5 |
| 2011/0003279 A1* | 1/2011 | Patel | 374/104 |
| 2011/0013668 A1* | 1/2011 | Pacha et al. | 374/178 |

FOREIGN PATENT DOCUMENTS

| | | |
|---|---|---|
| EP | 1 619 496 | 1/2006 |
| KR | 10-2005-0087955 | 9/2005 |
| KR | 10-2006-0089101 | 8/2006 |

* cited by examiner

*Primary Examiner* — G. Bradley Bennett

(74) *Attorney, Agent, or Firm* — Cantor Colburn LLP

(57) ABSTRACT

A method for identifying a biomolecule using a biomolecule detector having a field effect transistor (FET) is provided. The method comprises the steps of (a) heating a sample containing a biomolecule loaded in the detector to thereby elevate the temperature of the sample; (b) measuring electric current flowing through a channel formed between a source region and a drain region in the FET while raising the temperature in the step (a); (c) obtaining a transition temperature that is the temperature at maximum point of current variation from data measured in the step (b); and (d) identifying the biomolecule using the transition temperature obtained in the step (c).

10 Claims, 13 Drawing Sheets

Fig.2A
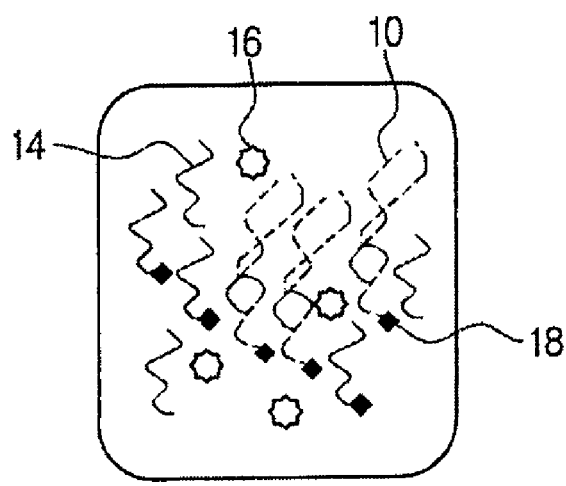
Mixture of PCR products
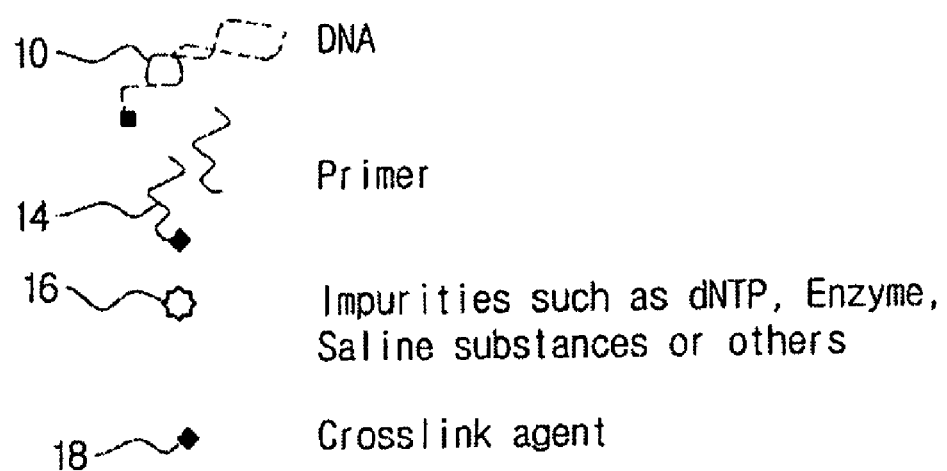

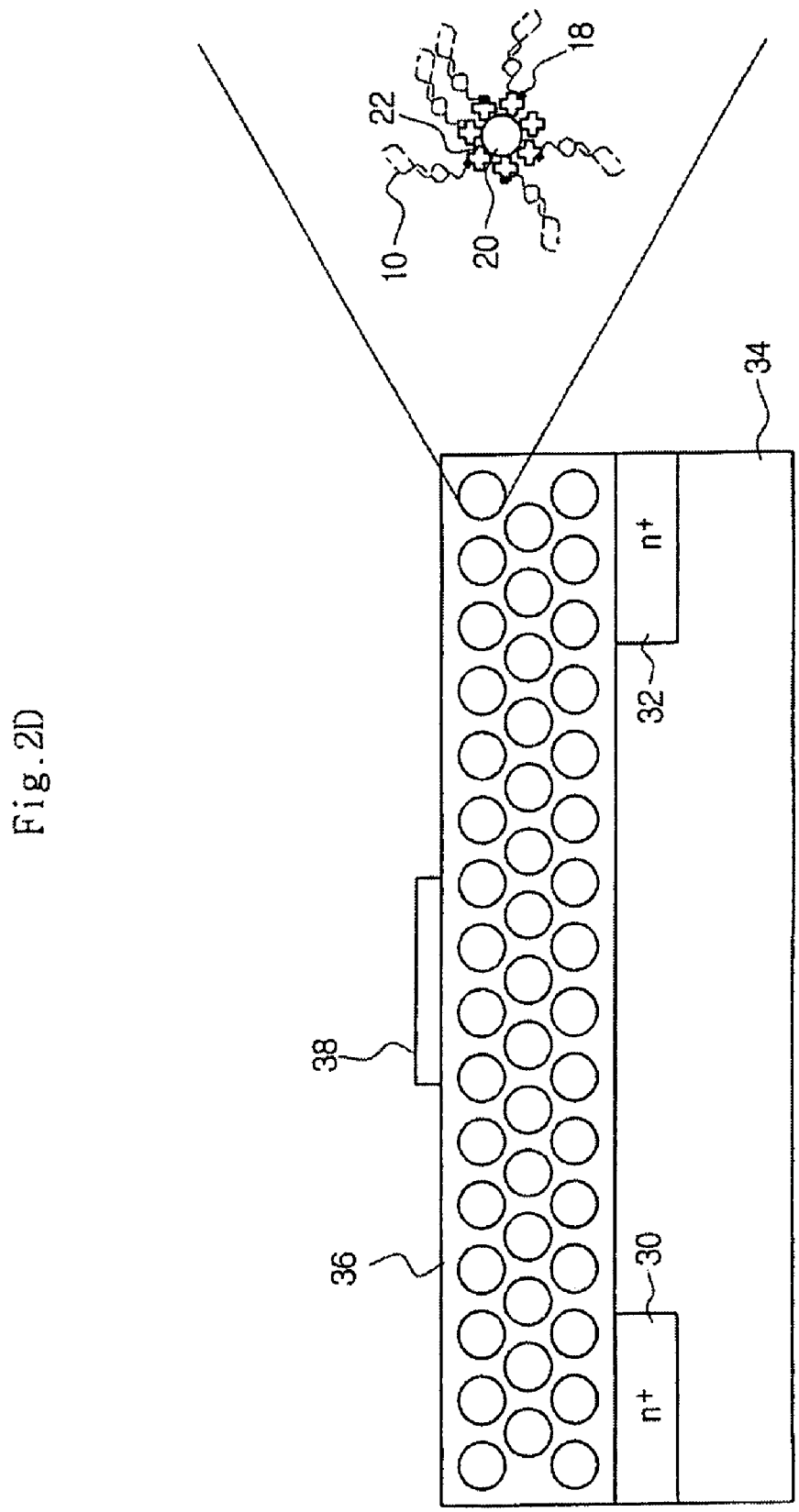

Fig.3
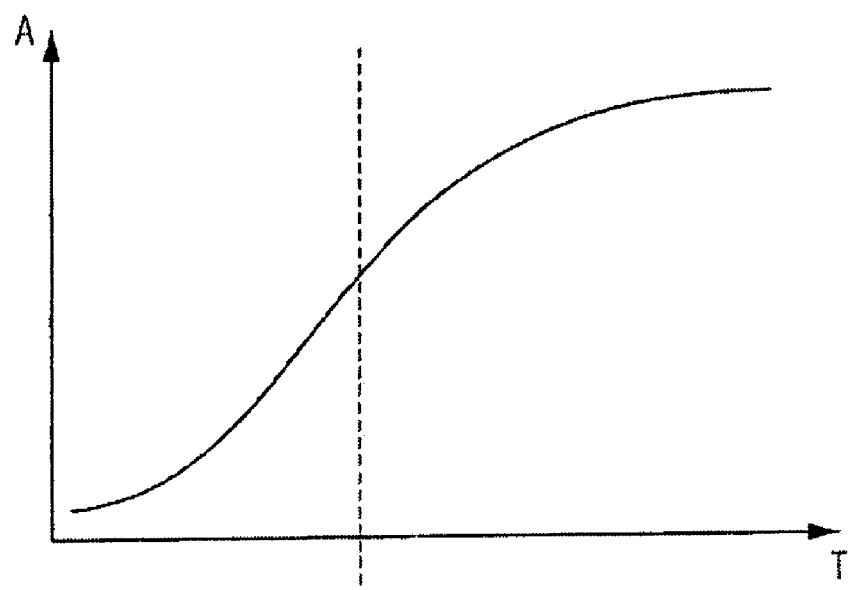
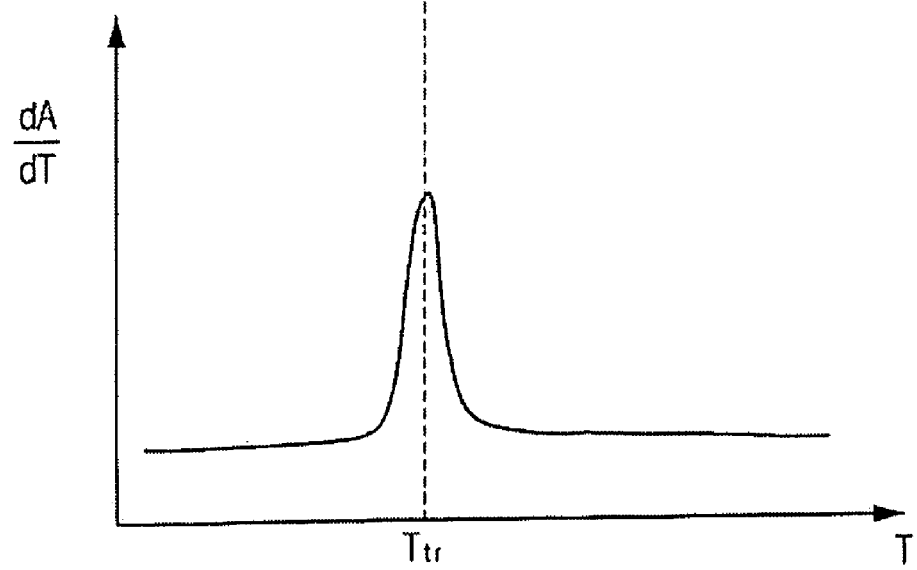

METHOD FOR IDENTIFYING A BIOMOLECULE

CROSS-REFERENCES TO RELATED APPLICATIONS

The present invention claims priority of Korean patent application number 10-2007-0113958 filed on Nov. 8, 2007, which is incorporated by reference in its entirety.

BACKGROUND OF THE INVENTION

1. Field of the Invention

The present invention relates to a method for identifying a biomolecule. More particularly, the present invention relates to a method for identifying a biomolecule using biomolecule detector having a field effect transistor (VET) capable of detecting a biomolecule.

2. Description of the Related Art

Researches about a transistor-based detector have been actively performed among detectors that with an electric signal, detect a biomolecule, e.g., a gene, such as DNA, RNA or Peptide Nucleic Acid (PNA). Since such a transistor-based detector is fabricated using a semiconductor process, the fabrication is easily done with grafting onto an integrated circuit or microelectromechanical system (MEMS) process. Further, in the transistor-based detector, a detecting result can be quickly known through the processing of the electric signals.

The representative one of the transistor-based detectors is an FET-based detector that measures biological reactions using an FET. The FET-based detector can be effectively used in a lap-on-a-chip (LOC; which is a technology of diagnosing diverse diseases at one time in a small chip), a Point of Care (POC) or the like through miniaturization in size.

SUMMARY OF THE INVENTION

The present invention is to provide a method for identifying a biomolecule using a biomolecule detector having a field effect transistor (FET).

Further, the present invention is to provide a recording medium having stored therein a program performing the above method for identifying a biomolecule.

In accordance with an aspect of the present invention, there is provided a method for identifying a biomolecule using a biomolecule detector having a field effect transistor (FET), the method comprising the steps of: (a) heating a sample containing a biomolecule loaded in the detector to thereby elevate the temperature of the sample; (b) measuring electric current flowing through a channel formed between a source region and a drain region in the FET while raising the temperature in the step (a); and (c) obtaining a transition temperature that is the temperature when a current variation is maximum from data measured in the step (b).

The method further comprises the step (d) of identifying the biomolecule using the transition temperature obtained in the step (c).

In accordance with another aspect of the present invention, there is provided a recording medium having stored therein a program and being readable in a computer for identifying a biomolecule using a biomolecule detector having a field effect transistor (FET), the program carrying out: (a) measuring electric current flowing through a channel formed between a source region and a drain region in the FET while raising the temperature of a sample containing a biomolecule loaded in the detector to thereby elevate the temperature of the sample; (b) differentiating the current data measured in the step (a) with respect to a temperature; (c) determining, as a transition temperature, the temperature at which a differential coefficient is maximum resulting from differentiation in the step (b); and (d) identifying the biomolecule using the transition temperature obtained in the step (c).

BRIEF DESCRIPTION OF THE DRAWINGS

The above and other objects, features and advantages of the present invention will be more apparent from the following detailed description taken in conjunction with the accompanying drawings, in which:

FIGS. 2A to 2F are views schematically illustrating a shape of a biomolecule or an adsorption medium in each process of the identifying method of the biomolecule according to an embodiment of the present invention;

FIG. 3 is a view for explaining a transition temperature at which the variation in current flowing through a channel of a field effect transistor (FET) is maximum in the identifying method of the biomolecule according to the embodiment of the present invention;

DETAILED DESCRIPTION OF THE PREFERRED EMBODIMENTS

Hereinafter, exemplary embodiments of the present invention will be described with reference to the accompanying drawings. The present invention however is not limited to the embodiments below.

Figure 1:
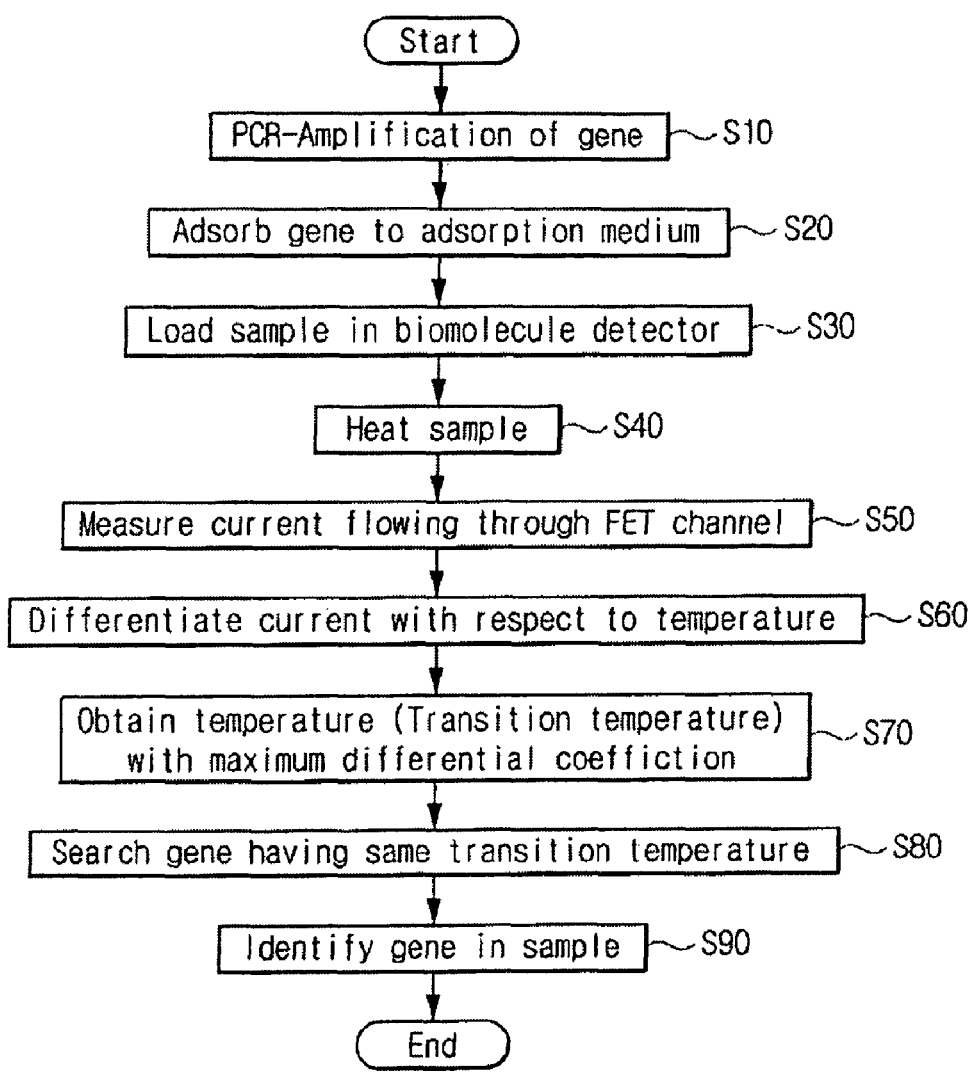
FIG. 1 is a flow chart illustrating a procedure of a method of identifying a biomolecule according to the present invention.

FIG. 1 is a flow chart illustrating a procedure of a method of identifying a biomolecule according to the present invention. FIGS. 2A to 2F are views schematically illustrating a shape of a biomolecule or an adsorption medium in each process of the identifying method of the biomolecule according to an embodiment of the present invention.

A method for identifying a biomolecule according to an embodiment of the present invention will now be explained referring to FIGS. 1 and 2A to 2F.

First, DNA is amplified using a PCR (S10). In the case of amplifying DNA, a sample containing a PCR product, as illustrated in FIG. 2A, also includes therein DNA 10, a primer 14 for use in PCR amplification, and impurities 16 such as dNTP, enzyme, saline substance and the others.

Here, the primer 14 is marked at the terminal region with a material, e.g., biotin, amine, epoxy, carboxyl acid, or tiol. These materials are cross-linked with an adsorption medium such that they are easily adsorptive to the adsorption medium such as beads. Thus, the marking materials attached to the terminal region of the primer will be called as crosslink agent herein.

Figure 2B:
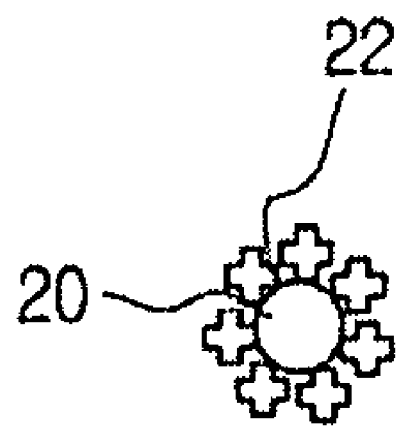
Figure 2C:
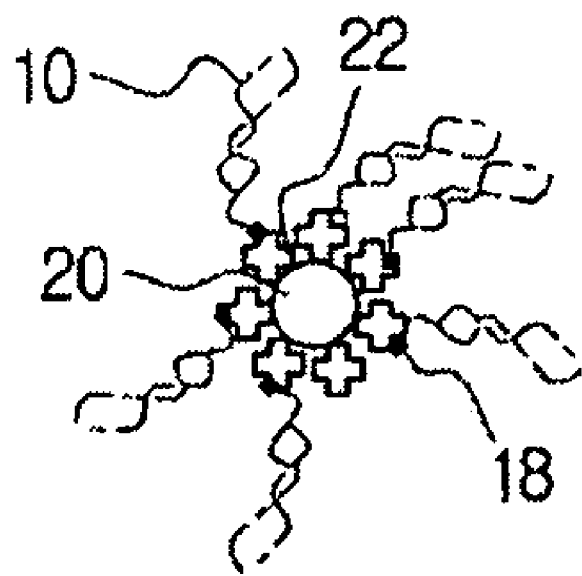

Then, the PCR product is mixed with the adsorption medium 20 as illustrated in FIG. 2B, so that DNA 10 in the PCR product is adsorbed to the adsorption medium 20 as illustrated in FIG. 2C (S20).

The adsorption medium 20 may be beads made of glass, silicon, plastic, gold, or magnetic substance.

Further, the adsorption medium 20 may be provided at the surface with an adsorption site 22 allowing DNA 10 to be easily adsorbed thereonto.

Then, the sample containing the beads 18 adsorbed with DNA 10 is loaded into a chamber 36 of the FET-based detector (S30).

Here, the FET-based biomolecule detector, as illustrated in FIG. 2D, includes a source region 30 and a drain region 32 formed on a semiconductor substrate spaced apart from each other, the chamber 36 formed on the semiconductor substrate 34 including the source and drain regions 30 and 32 and into which the sample containing the adsorption medium 20 adsorbed with DNA 10 is to be loaded, and an electrode 38 for applying voltage to the sample in the chamber 36.

When the sample is loaded in the chamber 36 and voltage is applied to the electrode 38, a channel is formed between the source and drain regions 30 and 32 and DNA 10 in the sample is detected by the quantity of current flowing through the channel.

Then, the sample in the chamber 36 is washed with a buffer solution to remove the impurities (e.g., dNTP, enzyme, saline substances and others) other than the beads 20 adsorbed with DNA 10.

The present embodiment has been constructed such that the beads 20 adsorbed with PCR-amplified DNA 10 are loaded in the chamber 36 of the detector (S30), and the sample is washed to thereby remove the impurities. Alternatively, it may however be constructed such that the DNA 10 adsorbed beads 20 are firstly washed to remove the impurities, and then the washed DNA 10 adsorbed beads 20 are loaded in the chamber 36 (S30).

Figure 2E:
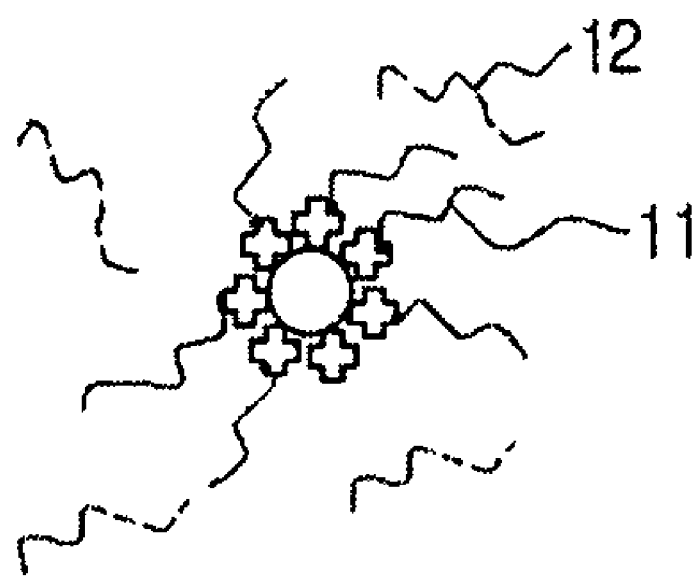

Next, the sample in the chamber 36 is heated to elevate the temperature of the sample above a melting point of DNA 10 (e.g., about 50 to 100° C.) (S40). Here, the elevation rate of temperature is kept constant (e.g., at 0.05° C./sec). When the temperature of the sample is higher than the melting point, DNA 10 in the sample is denatured so that a double strand structure thereof is released into a single strand structure as illustrated in FIG. 2E.

Thus, the single strand DNA 11 that was adsorbed on the bead 20 is still adsorbed thereon, whereas the other single strand DNA 12 complementary to the former DNA comes to freely move in the sample through the space (void) between the beads.

Meanwhile, while the sample is heated as such, the electric current flowing through the channel formed between the source region 30 and drain region 32 is measured using the biomolecule detector (S50).

Figure 2F:
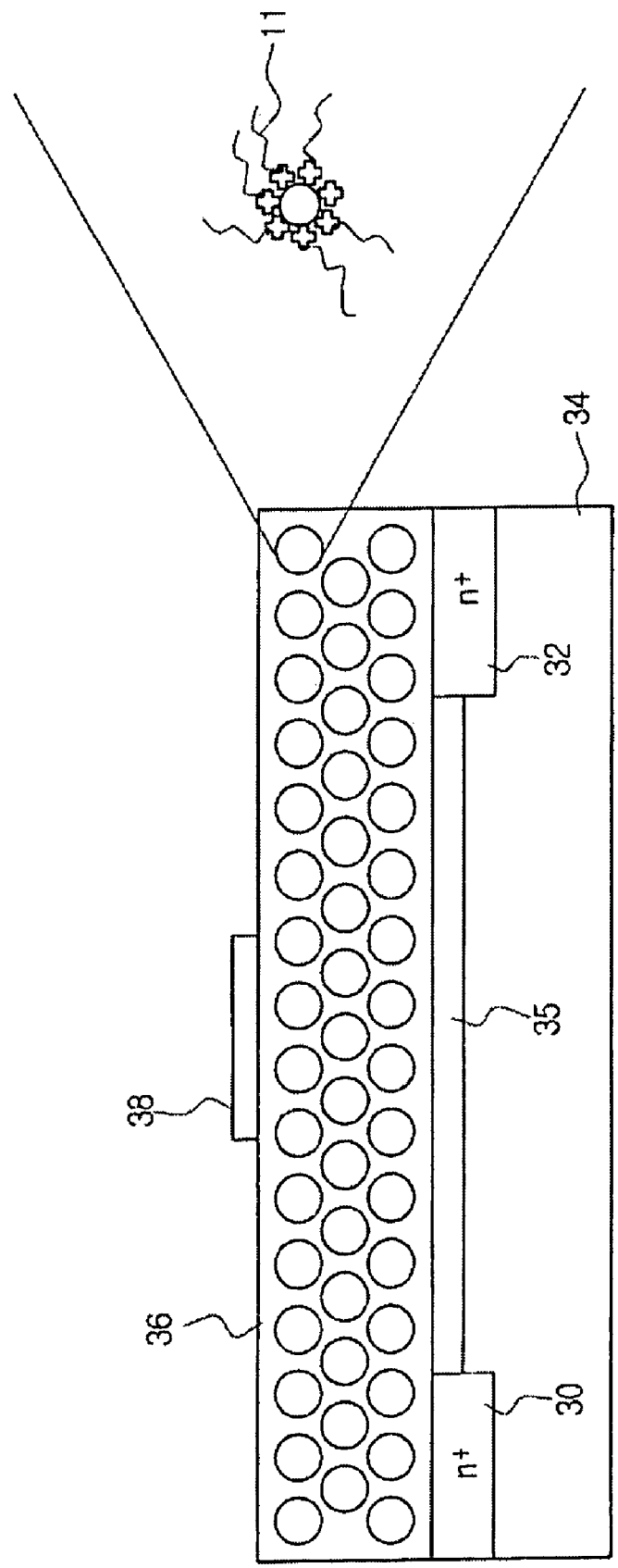

That is, as illustrated in FIG. 2F, voltage is applied to the electrode 38 so that the simple containing DNA 10 adsorbed beads 20 is applied with voltage. Mere, as the temperature of the sample rises, DNA 10 is denatured to create the single strand DNA 12. Electric current occurred between the source and drain regions 30 and 32 due to the single strand DNA 12. The measuring results of current flowing through the channel between the source and drain regions are shown in graphical diagram at upper side of FIG. 3.

Then, the measured current data is differentiated with respect to a temperature (S60). From the result of the differentiation, a transition temperature $T_{tr}$, the temperature at which a differential coefficient is maximum, is obtained (S70). The result of differentiating the measured current data with respect to the temperature (dA/dT) is shown in graphical diagram at lower side of FIG. 3. In the current (A)-temperature (T) graph of FIG. 3, it can be known that a point corresponding to the transition temperature ($T_{tr}$) corresponds to a inflection point where the differential coefficient (dA/dT) has a maximum value.

Even in the same DNA, the measured transition temperature can be different values depending upon the kind and the quantity of salts, etc. in the buffer solution used in a transition temperature measuring experiment. However, under the same environment and condition in the experiment, the same DNA has the same transition temperature.

Thus, using the transition temperature, it can be checked and identified the kind of DNA 10 in the PCR product.

To this end, the measuring of a transition temperature is done to DNAs (e.g., DNA of E. coli, etc.), a kind of which has already been known, using the same method under the same condition and environment as those of the steps (S10 to S70) to obtain inherent transition temperatures of the DNAs, thereby constructing a database.

Then, a search (S80) is done whether there is the biomolecule having the same transition temperature as that obtained in the steps (S70). If the searching result indicates the existence of the corresponding DNA, it can be known that the searched DNA is the same kind as that of DNA 10 amplified in the step (S10) (S90).

The FET of the biomolecule detector used in the embodiment is designed so as to detect the biomolecule in the sample through measuring the quantity of current in the channel 35. Alternatively, the detector may however be constructed so that the single strand DNA generated upon DNA denaturation is adsorbed onto a gate electrode of the FET to thereby measure the quantity of current in the channel.

Figure 4:
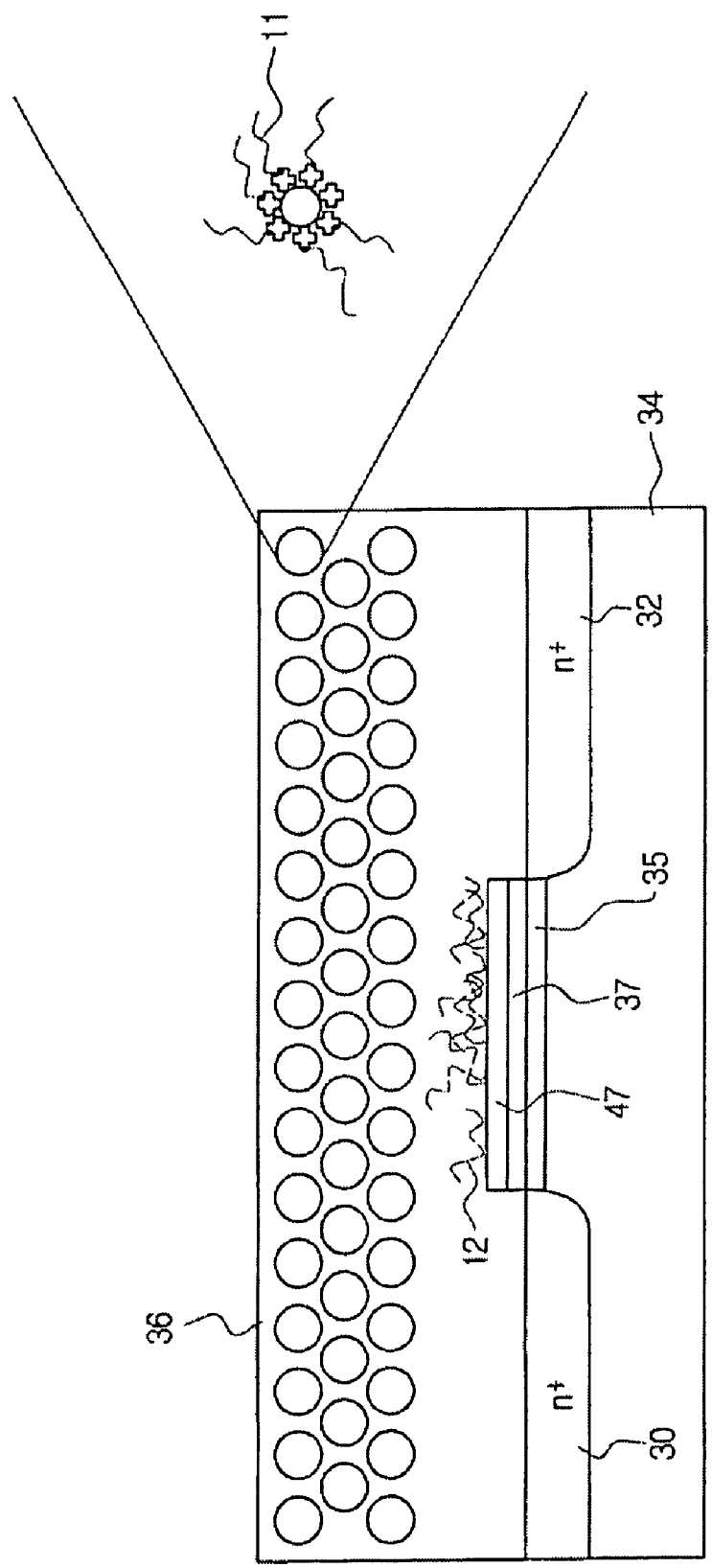
FIG. 4 is a view illustrating the construction of an FET-based biomolecule detector for use in an identifying method of the biomolecule according to another embodiment of the present invention.

FIG. 4 illustrates the construction of the biomolecule detector constructed as above. The biomolecule detector of FIG. 4 includes a source region 30 and a drain region 32 formed on a semiconductor substrate 34 spaced from each other; a gate electrode layer 37 formed between the source and drain regions 30 and 32; and a chamber 36 formed on the semiconductor substrate 34 including the gate electrode layer 37 and into which the sample containing DNA-adsorbed beads 20 is loaded. The gate electrode layer 37 is provided at the upper portion with a gate adsorption layer 47 onto which a gene is adsorbable.

Upon DNA denaturation, the single strand DNA 12 generated is adsorbed onto the gate adsorption layer 47 formed on the gate electrode layer 37, so that the channel 35 is formed between the source region 30 and drain region 32 and the quantity of current flowing through the channel increases.

Figure 5:
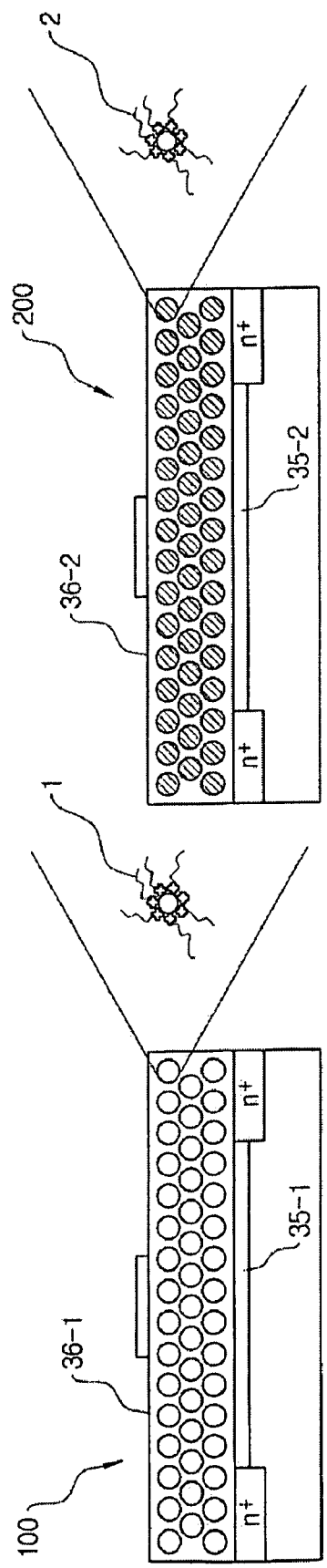
FIG. 5 is a constructional diagram of an experiment for detecting and identifying diverse kinds of biomolecules with different FET-based biomolecule detectors according to the present invention.

FIG. 5 is a constructional diagram of an experiment for detecting and identifying diverse kinds of PCR products 1 and 2 wherein the different PCR products 1 and 2 are respectively loaded in the chambers 36-1 and 36-2, that are correspond to the FETs 100 and 200 included in the biomolecule detector, and the transition temperature is obtained according to the present invention to thereby identify the respective PCR products 1 and 2.

Figure 6:
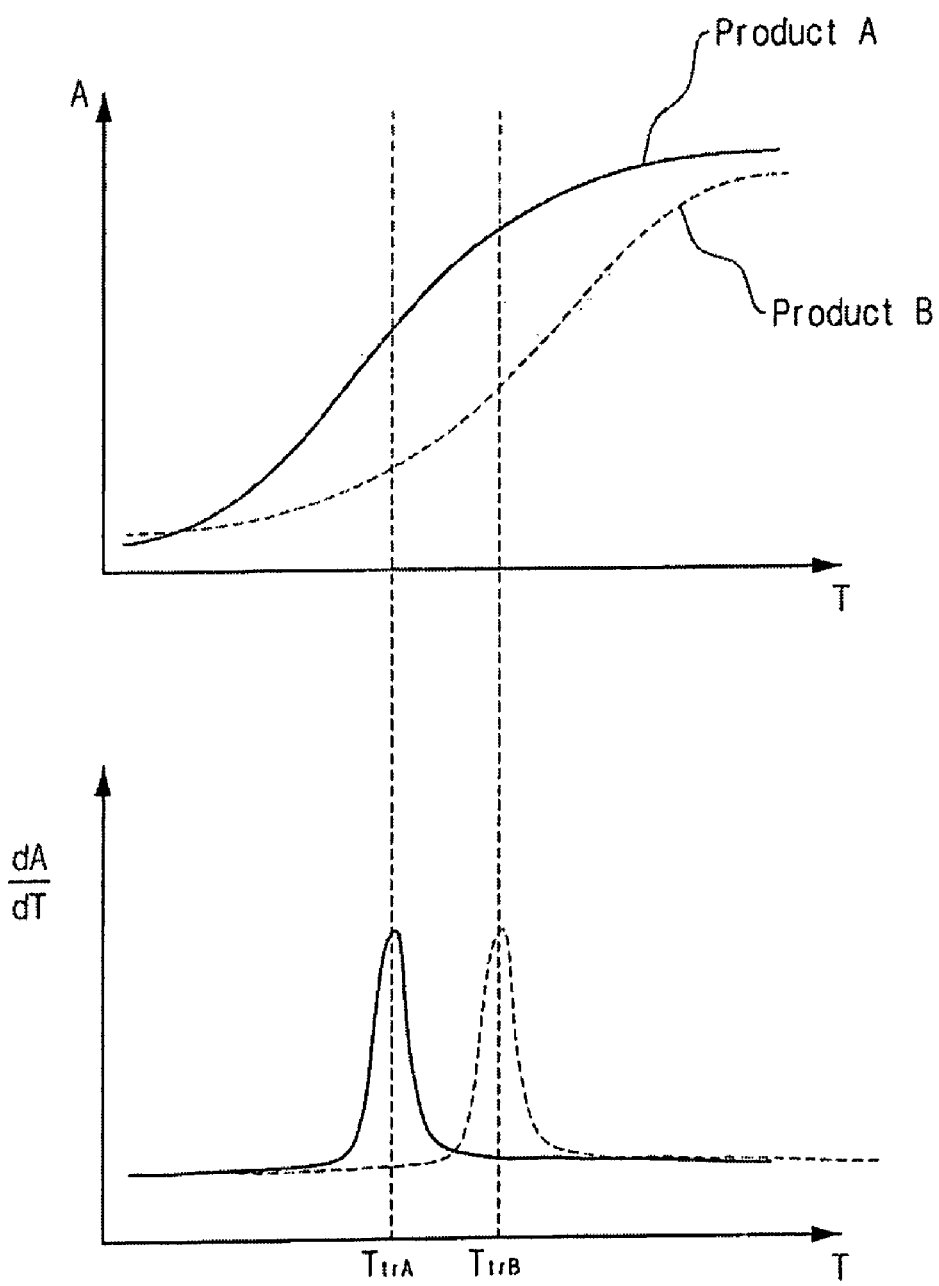
FIG. 6 is a graphical diagram illustrating a transition temperature obtained in the embodiment of FIG. 5.

The resulting current-temperature graph and the transition temperature that are measured from the experimental construction of FIG. 5 are shown in FIG. 6. Since the PCR product A (1) and the PCR product B (2) have different transition temperatures ($T_{trA}$, $T_{trB}$), the respective PCR products A and B can be identified using such transition temperature characteristics.

Figure 7:
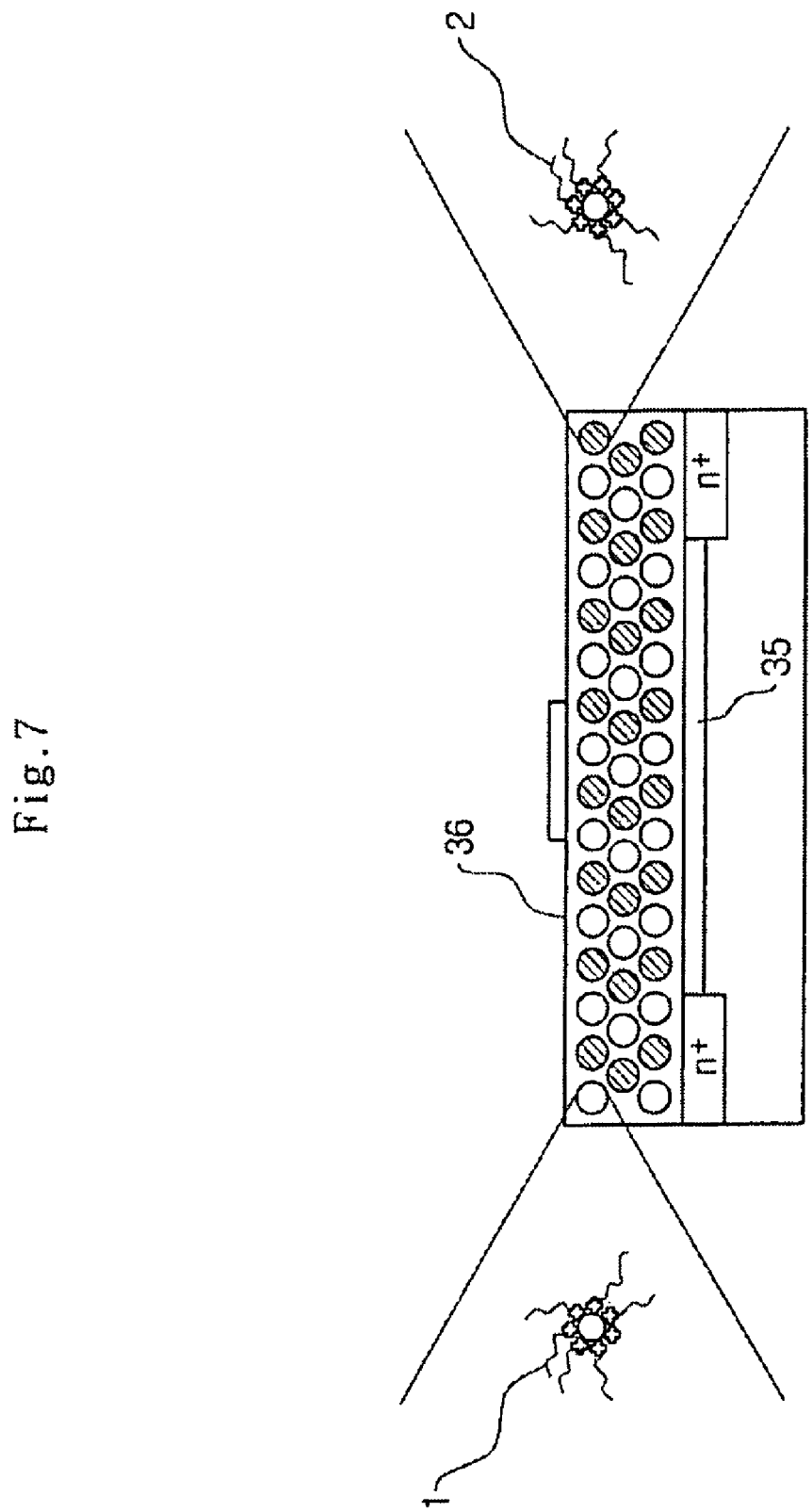
FIG. 7 is a constructional diagram of an experiment for detecting and identifying diverse kinds of biomolecules with the same FET-based biomolecule detector according to the present invention.

FIG. 7 is a constructional diagram of an experiment for detecting and identifying diverse kinds of PCR products 1 and 2 wherein the different PCR products 1 and 2 are loaded in a single chamber 36, and the transition temperature is obtained according to the present invention to thereby identify the respective PCR products 1 and 2.

Figure 8:
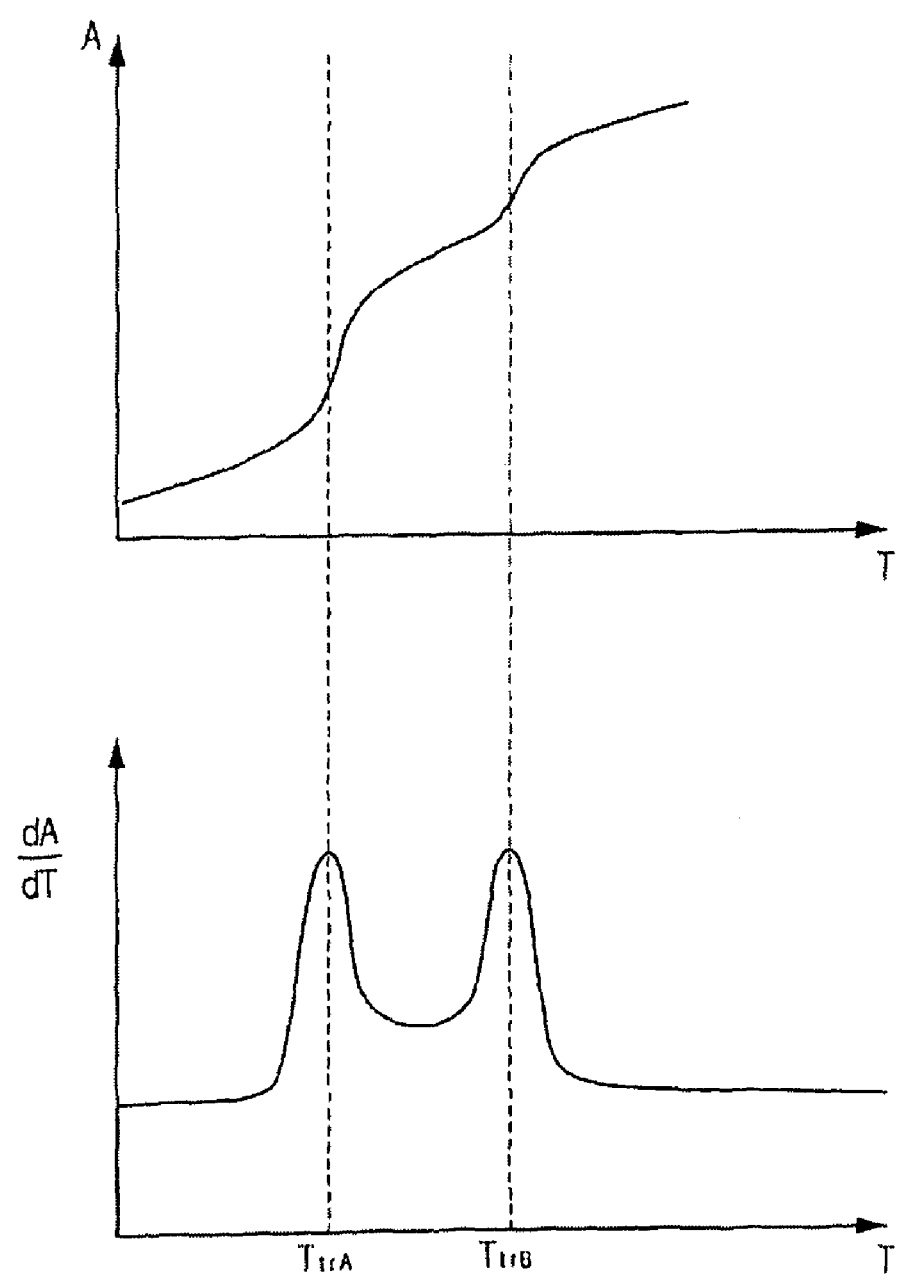
FIG. 8 is a graphical diagram illustrating a transition temperature obtained in the embodiment of FIG. 7.

The resulting current-temperature graph and the transition temperature that are measured from the experimental construction of FIG. 7 are shown in FIG. 8. The current flowing through the FET channel 35 is affected by both the PCR products A(1) and B(2). Thus, the differentiation value of the measured current with respect to the temperature has two maximum values, which respectively mean the transition temperatures ($T_{trA}$) of the PCR product A(1) and the transition temperatures ($T_{trB}$) of the PCR product B(2). The respective PCR products A and B can be identified using such transition temperature characteristics. Thus, although diverse kinds of DNAs are simultaneously PCR-amplified, the respective DNAs can be simultaneously identified from a single sample according to the present invention.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A method for identifying a biomolecule using a biomolecule detector having a field effect transistor (FET), the method comprising the steps of:
    (a) heating a sample containing a biomolecule loaded in the detector to elevate the temperature of the sample;
    (b) measuring electric current flowing through a channel formed between a source region and a drain region in the FET while raising the temperature in the step (a); and
    (c) obtaining a transition temperature that is the temperature at which a current variation is maximum.

2. The method according to claim 1, further comprising the step (d) of identifying the biomolecule using the transition temperature obtained in the step (c).

3. The method according to claim 1, wherein in the step (a), the biomolecule is adsorbed onto an adsorption medium.

4. The method according to claim 1, wherein the step (e) comprises:
    (c1) differentiating the current data measured in the step (b) with respect to a temperature; and
    (c2) determining, as a transition temperature, the temperature at which a differential coefficient is maximum.

5. The method according to claim 2, further comprising the step (e) of carrying out the steps (a) to (c) to a known biomolecule under the same condition as that of the biomolecule in the sample to thereby obtain the transition temperature of the known biomolecule.

6. The method according to claim 5, wherein the step (d) comprises
    (d1) searching a biomolecule having the same transition temperature as that of the biomolecule in the sample from the transition temperature data obtained in the step (e); and
    (d2) if the biomolecule having the same transition temperature as that of the biomolecule in the sample is searched in the step (d1), it is determined that the searched biomolecule is the same kind as that of the biomolecule in the sample.

7. The method for identifying a biomolecule according to claim 1, wherein the biomolecule detector comprises:
    a source region and a drain region formed on a semiconductor substrate spaced apart from each other;
    a gate electrode layer formed between the source and drain regions; and
    a chamber formed on the semiconductor substrate including the gate electrode layer and into which the sample containing a gene can be loaded,
    wherein a gate adsorption layer onto which the gene is adsorbable is formed on the gate electrode layer.

8. The method according to claim 1, wherein the biomolecule detector comprises:
    a source region and a drain region formed on a semiconductor substrate spaced apart from each other;
    a chamber formed on the semiconductor substrate and into which the sample containing a gene can be loaded; and
    an electrode for applying voltage to the sample in the chamber.

9. A recording medium storing a program for identifying a biomolecule using a biomolecule detector having a field effect transistor (FET), the program carrying out:
    (a) measuring electric current flowing through a channel formed between a source region and a drain region in the FET while heating a sample containing a biomolecule loaded in the detector to elevate the temperature of the sample;
    (b) differentiating the current data measured in the step (a) with respect to a temperature;
    (c) determining, as a transition temperature, the temperature at which a differential coefficient is maximum; and
    (d) identifying the biomolecule using the transition temperature obtained in the step (c).

10. The recording medium according to claim 9, wherein the step (d) comprises:
    (d1) carrying out the steps (a) to (c) to a known biomolecule under the same condition as that of the biomolecule in the sample to obtain the transition temperature of the known biomolecule;
    (d2) searching a biomolecule having the same transition temperature as that of the biomolecule in the sample from the transition temperature data obtained in the step (d1); and
    (d3) if the biomolecule having the same transition temperature as that of the biomolecule in the sample is searched in the step (d2), it is determined that the searched biomolecule is the same kind as that of the biomolecule in the sample.

* * * * *